United States Patent
Zuest et al.

[11] Patent Number: 6,030,219
[45] Date of Patent: Feb. 29, 2000

[54] DENTAL ATTACHMENT ASSEMBLY

[75] Inventors: Paul T. Zuest, Escondido; Scott Mullaly, San Marcos, both of Calif.

[73] Assignee: Zest Anchors, Inc., Escondido, Calif.

[21] Appl. No.: 09/170,585

[22] Filed: Oct. 13, 1998

[51] Int. Cl.⁷ ........................................... A61C 13/12
[52] U.S. Cl. .............................. 433/181; 433/172
[58] Field of Search ............................ 433/172, 173, 433/174, 181, 182, 191, 193, 194, 177, 178

[56] References Cited

U.S. PATENT DOCUMENTS

| | | | |
|---|---|---|---|
| 711,324 | 10/1902 | Lacy | 433/173 |
| 866,340 | 9/1907 | Roach | 433/177 |
| 3,514,858 | 6/1970 | Silverman | 433/174 |
| 3,787,975 | 1/1974 | Zuest | 433/182 |
| 3,991,472 | 11/1976 | Lukesch | 433/169 |
| 4,158,256 | 6/1979 | Wiland et al. | 433/219 |
| 4,290,755 | 9/1981 | Scott | 433/173 |
| 4,431,416 | 2/1984 | Niznick | 433/174 |
| 4,488,874 | 12/1984 | Soifer | 433/173 |
| 4,488,875 | 12/1984 | Niznick | 433/173 |
| 4,540,367 | 9/1985 | Sulc | 433/181 |
| 4,547,156 | 10/1985 | Hader | 433/172 |
| 4,626,213 | 12/1986 | Shiner et al. | 433/173 |
| 4,645,453 | 2/1987 | Niznick | 433/173 |
| 4,657,510 | 4/1987 | Gittleman | 433/173 |
| 4,738,623 | 4/1988 | Driskell | 433/173 |
| 4,780,080 | 10/1988 | Haris | 433/173 |
| 4,793,808 | 12/1988 | Kirsch | 433/173 |
| 4,832,601 | 5/1989 | Linden | 433/173 |
| 4,854,872 | 8/1989 | Detsch | 433/173 |
| 4,907,969 | 3/1990 | Ward | 433/173 |
| 4,932,868 | 6/1990 | Linkow et al. | 433/174 |
| 4,934,935 | 6/1990 | Edwards | 433/174 |
| 4,957,438 | 9/1990 | Bax | 433/180 |
| 4,988,297 | 1/1991 | Lazzara et al. | 433/173 |
| 5,007,835 | 4/1991 | Valen | 433/174 |
| 5,030,095 | 7/1991 | Niznick | 433/173 |
| 5,092,770 | 3/1992 | Zakula | 433/172 |
| 5,120,222 | 6/1992 | Sulc | 433/181 |
| 5,194,000 | 3/1993 | Dury | 433/173 |
| 5,195,891 | 3/1993 | Sulc | 433/173 |
| 5,211,561 | 5/1993 | Graub | 433/173 |
| 5,417,570 | 5/1995 | Zuest et al. | 433/177 |
| 5,520,540 | 5/1996 | Nardi et al. | 433/172 |
| 5,556,280 | 9/1996 | Pelak | 433/172 |
| 5,636,989 | 6/1997 | Somborac | 433/173 |
| 5,678,997 | 10/1997 | De Buck | 433/181 |

FOREIGN PATENT DOCUMENTS

| | | |
|---|---|---|
| 0 037 864 | 10/1981 | European Pat. Off. . |
| 3403 448 | 2/1984 | Germany . |
| WO 89/06941 | 8/1989 | WIPO . |

OTHER PUBLICATIONS

The Stern Era, A New Era in Attachment Dentistry Brochure, APM–Sterngold, 1990.

Primary Examiner—John J. Wilson
Assistant Examiner—Patrick A. Hilsmier
Attorney, Agent, or Firm—Brown, Martin, Haller & McClain, LLP

[57] ABSTRACT

A dental attachment assembly has an abutment member for attachment to a tooth root, implant, or adjacent tooth, and a male member for hinged engagement in a cap secured in a dental appliance. The male and abutment members are designed for releasable snap engagement to secure the members together. A skirt projects from the upper end of the male retention member and engages an outer locating surface of the abutment member as the members are secured together, acting to align the male member with the abutment members.

28 Claims, 5 Drawing Sheets

DENTAL ATTACHMENT ASSEMBLY

BACKGROUND OF THE INVENTION

The present invention relates to dental attachment or anchoring structures for attaching dental appliances such as overdentures, partial dentures, and the like to a remaining non-vital root, an adjacent tooth, or to an endosseus implant.

In U.S. Pat. No. 5,417,570 of Zuest et al., a dental anchor assembly is described in which a female part for attachment to a tooth root or implant has a socket, and a male part has a first end for snap engagement in the socket and a second end in swivel engagement in a cap for securing in a recess in a dental appliance. This provides for some relative movement at both ends of the male part, reducing the risk of excessive wear and loosening of the attachment.

It has been found that, in use, it is sometimes difficult for the wearer to properly locate the female socket, so that the mating, retentive end or head of the male part may hit the edge of the female part when the wearer inserts the denture. Repeated impacts of this type may damage the retentive head of the male, reducing or losing the retention force required for proper operation of the attachment.

Other prior art attachments utilize a male head which is in releasable snap engagement with a female socket, but do not provide a double hinging action since the male part is secured in the denture cap with no freedom of movement. Also, these arrangements do not always avoid the risk of damage to the retentive head of the male due to improper alignment with the female when re-inserting the denture or appliance. U.S. Pat. No. 5,195,890 of Sulc describes an attachment in which the cap and male are formed in one part, the cap having an integral, internal projection forming the male retentive head. U.S. Pat. No. 5,556,280 of Pelak describes an attachment system in which a male member is of cup-shaped structure, with an internal projection for snap-fit retention in the female socket. The male member is embedded in a receptacle or directly in the appliance.

SUMMARY OF THE INVENTION

It is an object of the present invention to provide a new and improved dental attachment assembly.

According to one aspect of the present invention, a dental attachment assembly is provided, which comprises a female socket member for attachment to a tooth root, implant, or adjacent tooth, the socket member having an upper end, a socket projecting inwardly from the upper end, and an outer locating surface portion projecting downwardly from the upper end, the outer locating surface portion being positioned to project above the tissue level when the socket member is secured in a tooth root or implant, a male retention member having an upper end comprising a swivel joint for swivel engagement in a recess in a dental appliance, a retention head projecting from the upper end for releasable snap engagement in the female socket, and a skirt projecting from the upper end of the male retention member surrounding the retention head, the skirt having a lower end for engaging the outer locating surface portion of the female socket member for aligning the retention head with the socket as the male retention member is secured to the female socket member.

Preferably, the skirt has an inner surface which is concave and does not contact the outer locating surface portion of the female socket member along the entire height of the attachment when the male and female members are secured together. The lower end of the skirt preferably projects below the retention head so that it will contact the locating surface portion of the female socket member prior to the retention head, reducing or avoiding the risk of damaging the head.

The outer locating surface portion of the socket member may have an outward taper for better centering of the male retention head. Alternatively, the outer locating surface portion of the female or socket member and the corresponding inner surface of the skirt of the male retention member may have corresponding snap engaging formations so that the skirt snaps into releasable locking engagement over the locating surface. In one embodiment, the locating surface has an outwardly bulging upper portion, while the inner surface of the skirt has a corresponding concave ring portion for snap engagement over the upper portion. This provides outside as well as inside snap retention of the dental appliance on the female member. This will reduce wear and increase the lifetime of the attachment. Alternatively, in this case, the inner snap engagement may not be needed, and the retention head and corresponding socket may be eliminated.

In a preferred embodiment of the invention, the outer locating surface portion of the female socket member has formations such as a pair of diametrically opposed notches for engagement with an insertion tool for engaging the female member with a tooth root or implant. A weep hole preferably connects the socket to the outside of the female member for allowing saliva to escape and reducing hydraulic pressure resulting from the male engagement in the female socket.

The female socket member may form an angled abutment for anchoring to implants extending at various implants. The angled abutment has a lower, connecting portion for securing the socket member to an implant or tooth root, the lower portion having a first axis, and an upper portion in which the socket is located, the socket having a second central axis at an angle to the first axis. Abutment members at various angles are provided.

According to another aspect of the invention, an attachment assembly is provided for securing a dental appliance in a gap adjacent to an abutment tooth. The assembly comprises a female socket member having an upper end, a socket projecting downwardly from the upper end, an attachment extending to one side of the socket for securing the socket member to a tooth, the socket member having an outer locating surface portion projecting downwardly from the upper end, a male retention member having an upper end comprising a swivel joint for swivel engagement in a recess in a dental appliance, a retention head projecting from the upper end for releasable snap engagement in the female socket, and a skirt projecting from the upper end of the male retention member surrounding the retention head, the skirt having a lower end for engaging the outer locating surface portion of the female socket member for aligning the retention head with the socket as the male retention member is secured to the female socket member. The skirt and locating surface may be designed for releasable snap engagement with one another for better retention.

According to another aspect of the invention, a dental attachment assembly is provided which comprises a first member for attachment to a tooth root, implant, or adjacent tooth and a second member having an upper end comprising a swivel joint for swivel engagement in a recess in a dental appliance. The first member has an upper end and an outer locating surface portion positioned to project above the tissue level when the first member is secured to a tooth root, implant, or adjacent tooth. The second member is generally cup-shaped and has an upper end and a skirt depending downwardly from the upper end for engagement over the outer locating surface portion of the first member, the skirt having an inner surface, the inner surface of the skirt and outer locating surface portion of the first member having mateable, snap-engaging formations so that the skirt can be releasably snap engaged over the first member.

In a preferred embodiment of the invention, the first member has an outward bulge extending around its periphery adjacent its upper end, and the inner surface of the skirt has a corresponding annular, inward concavity for snap engagement over the bulge. This provides an outside snap retention of the male or second member over the first or female member. Additionally, the skirt will readily locate the female member and will self-center for snap engagement.

In addition to the outside snap retention, the first or female member may also be provided with an upwardly facing socket, and the second or male member may have a retention head projecting downwardly from the upper end for snap engagement in the socket as the skirt snaps over the outside. This combined inside and outside snap gives much better retention than just inner snap retention, and reduces wear problems. The outside snap will still provide retention even when the inner snap engaging surfaces wear out. This could potentially double the lifetime of an attachment.

The attachment assembly of this invention provides a downwardly depending skirt surrounding the male retention head, in combination with an outer locating surface portion on the female socket member which projects above the tissue level. The skirt and locating surface together act to align the connection of the male and female members and reduce the risk of damaging the male retention head on making the connection.

BRIEF DESCRIPTION OF THE DRAWINGS

The present invention will be better understood from the following detailed description of some preferred embodiments of the invention, taken in conjunction with the accompanying drawings in which like reference numerals refer to like parts and in which.

DESCRIPTION OF THE PREFERRED EMBODIMENTS

Figure 1:
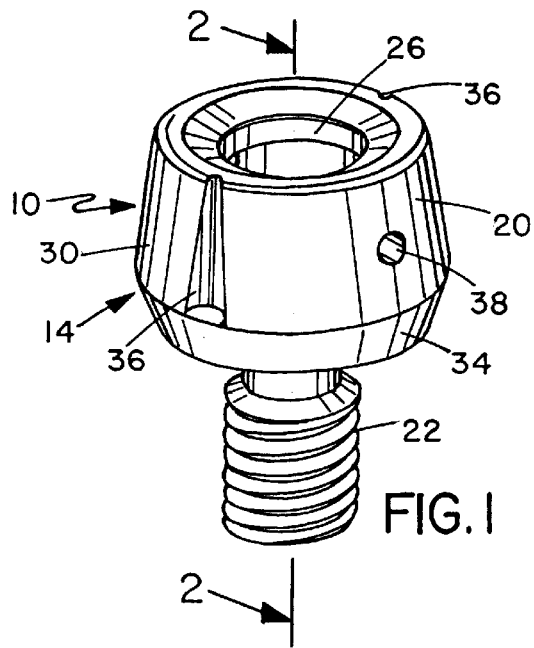
FIG. 1 is a perspective view of a preferred configuration of a female element of the dental attachment assembly according to a first embodiment of the invention.

FIGS. 1 to 4 of the drawings illustrate a dental attachment assembly 10 for attaching a dental appliance to an implant 12. The assembly basically comprises a female socket member or abutment element 14 and a male retention member or element 16 which has a swivel engagement in a cap 18 secured in a dental appliance.

The female element 14 is of relatively strong material such as titanium coated with titanium nitride, or similar material. Element 14 has an enlarged upper end portion 20 having an upwardly facing socket 26, and a downwardly depending threaded shaft or stem 22 for attachment to an implant fixture 12 secured in the bone of an upper or lower dental arch. In FIGS. 1 to 4, the stem 22 is threaded for engagement in a threaded cavity in an implant fixture 12. It will be understood that the female element will be provided in multiple thread configurations and diameters for engagement in any of the various implant fixtures currently available on the market.

Figure 4:
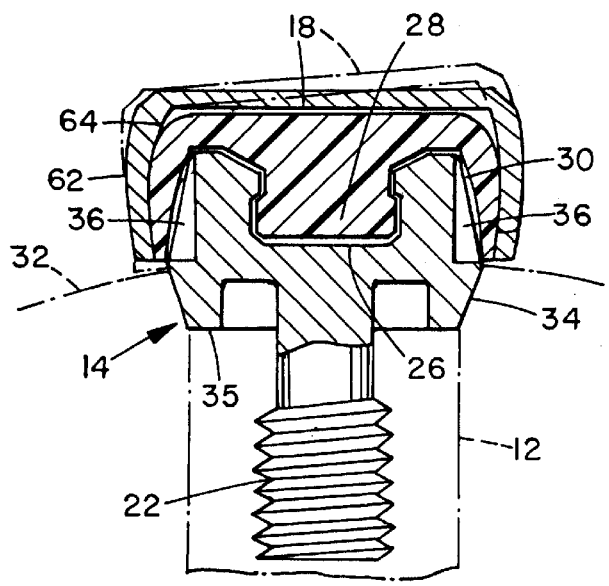
FIG. 4 is a similar view with the elements seated, with the male element hingedly connected to a cap.

The upwardly facing socket 26 is of suitable shape and dimensions for releasable snap engagement with a downwardly depending retention head 28 on the male element 16. The mating shapes of the socket 26 and head 28 are similar to that described in U.S. Pat. No. 5,417,570 of Zuest et al., the contents of which are incorporated herein by reference, and will have a similar action. An outer locating surface 30 of the upper end portion 20 projects upwardly above the tissue level 32 when the female element is secured to an implant or tooth root, as best illustrated in FIG. 4. Locating surface 30 preferably has a slight inward taper from a position just above the tissue level up to the upper end of end portion 20. The surface portion 34 below the gum level may be cylindrical or have a slight inward taper such that the diameter at the lower end 35 of upper end portion 14 matches that of the implant 12, as indicated in FIG. 4.

Figure 2:
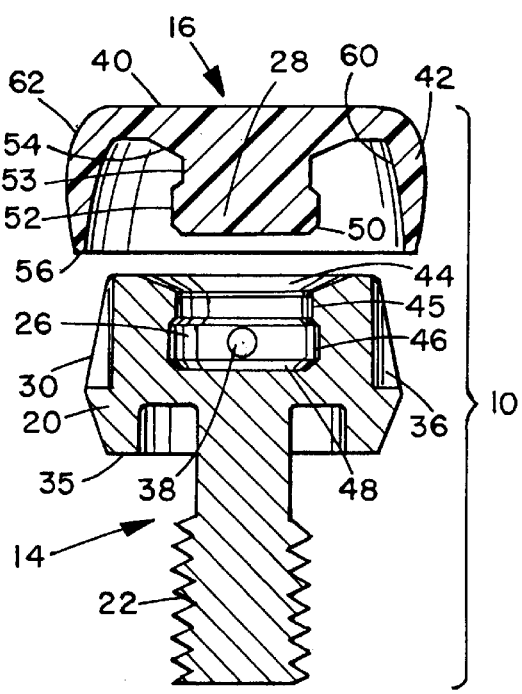
FIG. 2 is a sectional view taken on line 2—2 of FIG. 1, with the male element shown separated.

A pair of diametrically opposed, axially extending notches 36 are provided on the locating surface 30. These are designed for engagement with an insertion tool (not illustrated) for holding the implant or female element 14 and threading it into a matching socket in an implant fixture 12. The female element or abutment 14 also has a weep hole 38 connecting the socket 26 to the outer surface of element 14, as best illustrated in FIGS. 1 and 2.

The male element 16 is of a material having some resilience, preferably nylon plastic, and is generally cup-shaped. The upper surface 40 is generally flat, and a skirt 42 projects downwardly from the upper surface 40 to surround the retention head 28. The retention head 28 has an outer shape substantially matching that of the socket 26. Socket 26 has a tapered leading edge or rim 44, a reduced diameter portion 45, an enlarged ring groove portion 46, and a lower chamfer edge portion 48. Head 28 of the male element has a matching shape with a chamfer 50 at the lower end, an annular ring portion 52 of enlarged diameter for snap engagement in groove portion 46, a reduced diameter portion 53, and an outwardly tapered upper end portion 54.

Figure 3:
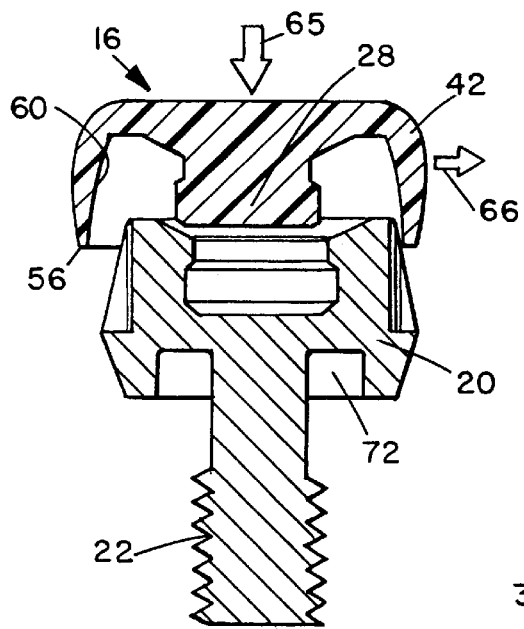
FIG. 3 is a view similar to FIG. 2, showing the self-alignment action.

The skirt 42 has a lower end 56 which projects below the lower end of head 28, and an inner surface 60 which is tapered, preferably at an angle of around 10°, and is also concave, as best illustrated in FIG. 4. The dimensions of the skirt and the head are such that the lower end 56 of the skirt will contact locating surface 30 before the lower end of the head contacts the female element, as best illustrated in FIG. 3. The outer surface 62 of skirt 42 is convex or rounded, for snap-fit, swiveling engagement in a cavity 64 of corresponding shape in the cap 18, as best indicated in FIG. 4. This provides a swiveling, rotational movement or hinging action at the cap, where the attachment is secured to the denture or appliance, reducing wear, in a similar manner to that described in U.S. Pat. No. 5,417,570 referred to above. The pivoting of the nylon or resilient male in the metal denture cap 18 allows minor corrections for non-parallel abutments, as well as providing a longer lasting, resilient connection.

The denture or appliance can be removed repeatedly for cleaning, simply by snapping male head 28 out of socket 26, and can then be re-inserted. On re-insertion in the direction of the arrow 65 in FIG. 3, for example, the user may fail to align head 28 co-axially with socket 26. In this case, the lower end of skirt 42 will contact one side of the locating surface 30 before the head 28 reaches the socket. Further downward movement in the direction of the arrow 65 urges the male element to one side, in the direction of arrow 66, to align head 28 properly with the socket. Thus, the locator surface portion 30 of the female element together with the inner locating surface of skirt 42 act to urge the head 28 into proper alignment with the socket prior to snap insertion in the socket. This avoids the problem of the nylon head potentially hitting the tapered rim 44 of the socket if mis-aligned, which would eventually cause damage to the softer head and decrease retention ability. The skirt and locator surface also allow easier location and insertion of the dental prosthesis by the patient.

The female element 14 will be provided in several tissue cuff heights to match the surrounding gingival level 32. The minimum height of the overall attachment assembly is much lower than that of the previous arrangement as described in U.S. Pat. No. 5,417,570 referred to above. The minimum height for a non-hexed implant abutment will be of the order of 1.75 mm., while the minimum height for a hexed implant abutment will be around 2.75 mm, which will help in cases where the implant is at tissue level. This is lower than the height of all such attachments currently on the market today, and has the advantage of providing a much lower profile and increased patient comfort. Other heights will also be provided depending on the depth of the tissue. The low profile above the attachment is also better for tooth placement.

By providing external notches 36 for engagement with an insertion tool, rather than an internal hex indent or the like as in U.S. Pat. No. 5,417,570, the height of the female element can be reduced. The notches allow the female element to be held firmly for threading into the implant fixture 12.

The weep hole 38 is located above the tissue level and makes it easier for saliva to escape from socket 26, reducing hydraulic pressure as a result of the male head engaging in the socket. This also allows easier connection of the male and female elements.

Once the head 28 is in snap engagement in the socket, as in FIG. 4, the skirt will only contact the locator surface portion 30 at the lower end, while the concave inner surface 60 will be spaced from surface portion 30 along the remainder of the attachment, as best illustrated in FIG. 4. This also enables easier insertion of the head 28 into the socket once the parts are in proper alignment.

Figure 5:
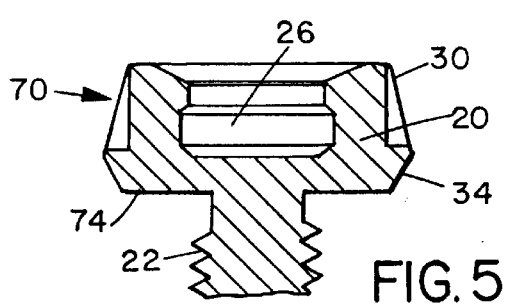
FIG. 5 is a sectional view showing a shortened form of the female element.

FIG. 5 illustrates a modified female element or abutment 70 for attachment to a non-hexed implant (not illustrated). Element 70 will be used with the male element 16 of FIGS. 1 to 4 in a similar manner to hexed implant abutment 14, and like reference numerals have been used for like parts as appropriate. In this embodiment, head portion 20 in FIG. 5 is shorter than in the previous embodiment, and the hex indent 72 of FIGS. 1 to 4 is eliminated, with head portion 20 instead having a flat, lower annular face 74 which fits against the flat upper face of the implant.

Figure 6:
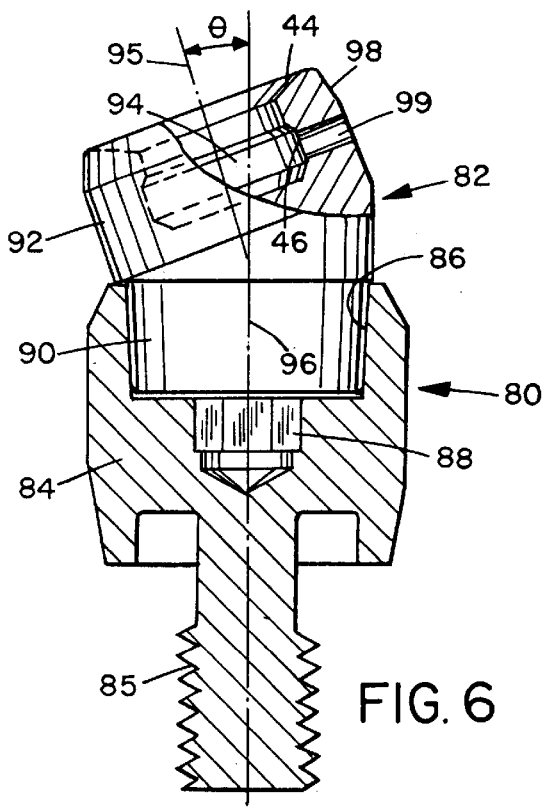
FIG. 6 is a sectional view showing an angle correction abutment.

FIG. 6 illustrates the female or abutment of a modified attachment assembly according to another embodiment of the invention, for use when an angle correction is necessary due to a divergent implant. The male element of this assembly will be identical to that of FIGS. 1 to 4. In this assembly, a two part female or abutment 80, and 82 is used. The lower part 80 has a cylindrical head portion 84 with a downwardly depending stem 85 which is suitably threaded and dimensioned for engagement in an implant of any standard type. Head portion 84 has a tapered, upwardly facing socket 86 with a hex or multi-sided recess 88 at its lower end for engagement with an appropriate insertion tool for threading the part 80 into an implant.

The upper part 82 of the abutment has a tapered lower surface portion 90 which has a precision machined taper known as a Morse taper which precisely matches the taper of socket 86, so that when portion 90 is forced into socket 86, the parts 80 and 82 will be permanently locked together. Upper part 82 has an angled upper portion 92 which has an axis at a predetermined angle to the lower portion 90. Upper parts 82 may be provided in a variety of different angles for accommodating different angular offsets in the implant. Preferably, upper parts 82 with angles of 10° and 20° are provided.

An upwardly facing socket 94 is provided in the angled upper portion 92 of the part 82 for releasable snap engagement with the head 28 of the male element of FIGS. 1 to 4. The shape and dimensions of the socket 94 are identical to that of socket 26 of the previous embodiments, and like reference numerals have been used for like parts as appropriate. However, unlike the previous embodiment, socket 94 has a central axis 95 which is at a predetermined angle θ to the attachment axis or direction 96, as indicated in FIG. 6. As noted above, parts 82 are preferably provided with angles of 10° and 20°.

With this embodiment, as in the previous embodiments, a tapered locator surface portion 98 is provided on part 82 for engaging the lower end 56 of skirt 42 of the male element 16 as the male element is re-attached by the patient. Thus, the same alignment occurs when the male element 16 is attached to an angle correction, two part female 80, 82 as described above in connection with FIG. 3. Also as in the previous embodiment, a saliva weep or bleed hole 99 connects the socket 94 with the outside of female part 82.

Figure 7:
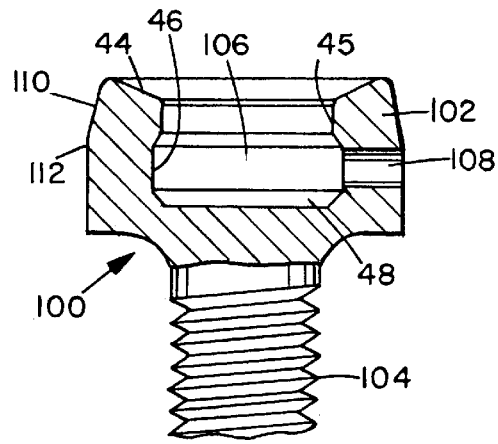
FIG. 7 is a sectional view of a root anchor attachment.

FIG. 7 illustrates another modified female element 100 which is also designed for releasable snap engagement with the male element 16 of FIGS. 1 to 4. The female element or attachment 100 is designed for direct cemented engagement in a prepared bore in a tooth root, rather than for threading into an implant as is the case with female elements 14 and 80, 82 referred to above.

Female element 100 has a head portion 102 and a reduced diameter, downwardly depending stem or shaft 104 which will typically be longer than the shaft of the female element 14 of the previous embodiment. The longer shaft or post 104 will add stability to the attachment. Shaft 104 is suitably threaded or provided with other formations for cement retention in a prepared bore in a tooth root. The head portion 102 has a socket 106 of identical shape and dimensions to that of FIGS. 1 to 4, and like reference numerals have been used for like portions as appropriate. Additionally, a saliva bleed hole 108 connects socket 106 to the outside surface of the element 100.

A tapered locator surface 110 is provided which extends from the upper end of head portion 102 downwardly to a location 112 which will be above the gum line when the female element is installed in a prepared root. As in the previous embodiments, when a patient attempts to re-attach a male element 16 to female element 100, the lower end 56 of the skirt 42 will first contact locator surface 110, and will be urged into a centrally aligned position as the patient contiues to urge the element downwardly. Thus, the retention head 28 will be properly aligned for snap engagement in socket 106.

Figure 8:
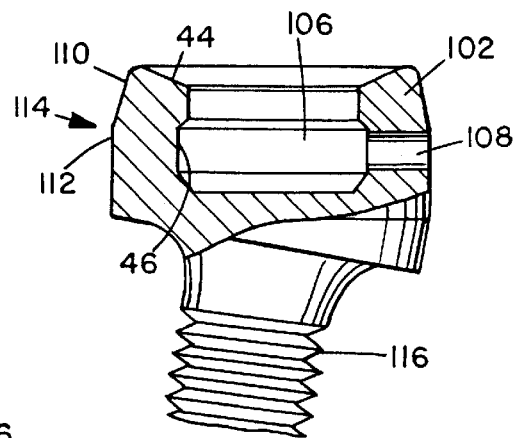
FIG. 8 is a view similar to FIG. 7, with an angle correction configuration.

FIG. 8 illustrates a modified root anchor or female element 114 which is similar to that of FIG. 7 but which is provided with an angle offset to accommodate divergent tooth roots. Female element 114 has a head portion 102 identical to that of the previous embodiment, and like reference numerals have been used for like parts as appropriate. A stem 116 projects downwardly at an angle to the axis of head portion 102. Female elements 114 may be provided with stems at various angles to accommodate different root divergence angles, and female elements 114 are preferably provided at angles of 10° and 20°.

The root anchors of FIGS. 7 and 8 are provided with a long stem which may be shortened by cutting to the appropriate length to conform to various lengths of root tips. Additionally, an alternative version of the root anchor may be provided which is identical to that of FIG. 7 but with no stem. This may be provided in plastic, and may be cast with a gold coping covering the exposed superior surface of the root, or with a cast bar on implants.

Figure 9:
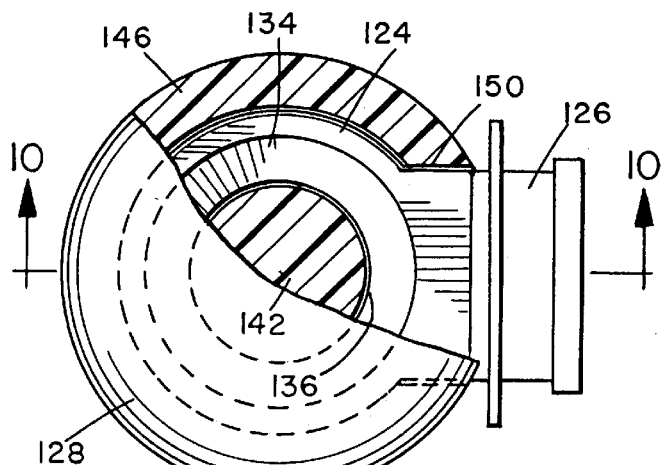
FIG. 9 is a top plan view, partially cut away, of a partial denture attachment assembly according to another embodiment of the invention.
Figure 10:
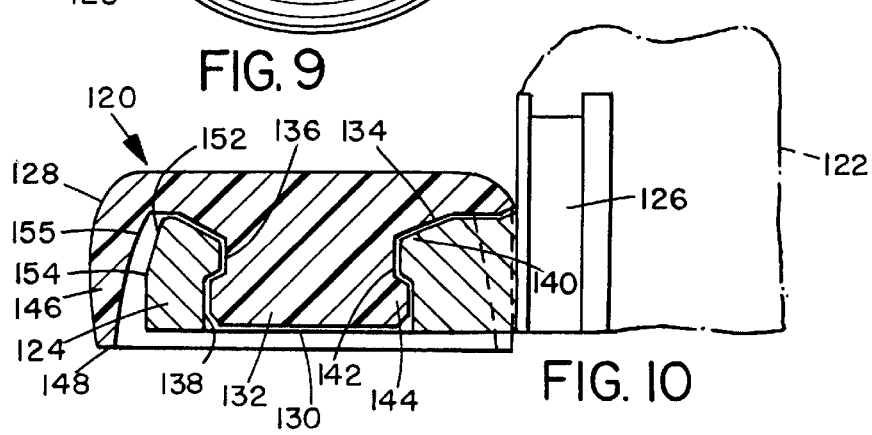
FIG. 10 is a sectional view taken on line 10—10 of FIG. 9.

FIGS. 9 and 10 illustrate a denture attachment or anchor assembly 120 according to another embodiment of the invention. The attachment assembly in this case is designed for attachment to an abutment tooth 122, rather than to a tooth root or implant. The assembly 120 basically comprises a female element 124 having a distal extension 126 which is secured in a suitable slot provided in an adjacent or abutment tooth 122, and a male element 128 for releasable snap engagement with female element 124.

Female element 124 has a through bore 130 which is shaped for releasable snap engagement with a retention head 132 of male element 128. Through bore 130 has a tapered rim portion 134, a reduced diameter portion 136, and an enlarged annular groove portion 138 at the lower end of the bore. Head 132 is of substantially matching shape, having a tapered portion 140, reduced diameter stem portion 142, and an enlarged ring portion 144 at the lower end for snap engagement in groove portion 138, as illustrated in FIG. 10. As in the previous embodiments, the female element is of a suitable cast metal or cemented metal insert while the male element is of resilient material such as nylon.

Male element 128 is generally cup shaped, with a downwardly depending skirt 146 surrounding head 132 and having a lower end 148 spaced below the lower end of head 132. Skirt 146 has a slot 150 for engaging over distal extension 126 of the female element when the parts are secured together, as best illustrated in FIG. 9.

As in the previous embodiments, female element 124 has an outwardly tapered, locating surface portion 152 projecting from the upper end of the element 124 downwardly to point 154. Element 124 is cylindrical from point 154 down to the lower end of the element. The skirt 146 has a concave inner surface portion 155 similar to surface portion 60 of the first embodiment.

The male element 128 of this embodiment will be hinged in a cavity in a suitable cap, as in the previous embodiment, and the cap will be secured in a dental appliance which is attached in the patient's mouth via male and female attachment assembly 120. As in the first embodiment, when a patient attempts to re-insert the appliance, the male head 132 may not be accurately aligned with the female socket element 124. In this case, the lower end 148 of skirt 146 will hit the locator surface 152, as indicated in FIG. 3 for the first embodiment, and further downward force will tend to urge the male element sideways until it is in proper alignment with bore 130. The male head 132 can then be pushed down easily into snap engagement in bore 130, into the position illustrated in FIG. 10.

In each of the previous embodiments, the female element or abutment has an upper locator surface which is tapered. The taper angle is preferably of the order of 10°. The inner surface of the skirt on the male member has a similar taper, but is concave such that the opposing surfaces are spaced apart when the male is fully engaged.

Figure 11:
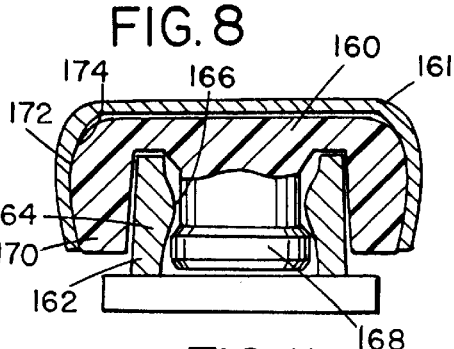
FIG. 11 is a sectional view of a retrofit configuration.

FIG. 11 illustrates a modified male element 160 and cap 161 which may be used for retrofit into an existing female or anchor 162 of the type which is generally cup shaped having an upstanding cylindrical wall 164. The inner surface of wall 164 has an annular, rounded rib 166. This type of female anchor is well known in the field. In this embodiment, the male element 160 of the attachment assembly is modified for snap engagement with a female anchor of the type illustrated in FIG. 11. As in the previous embodiments, male element 160 is of a suitable, durable resilient material such as nylon plastic.

The male element 160 is also generally cup-shaped, with a retention head 168 of similar shape to the previous embodiments and a downwardly depending peripheral skirt 170. However, unlike the previous embodiments, skirt 170 does not extend below the lower end of head 168.

Male element 160 has an outer curved surface 172 which is designed for hinged engagement in a correspondingly shaped cavity 174 in the metal cap 161, as in the first embodiment. In this embodiment, the male hinges at one end in cap 161 which is secured in the dental appliance. The appliance may be removed for cleaning purposes by snapping head 168 out of the bore in female element 162. It may be re-inserted by forcing head 168 downwardly until it snaps past rib 166 into the engaged position illustrated in FIG. 11.

The attachment will then have some freedom of movement at both ends, both at the cap and at the female element, reducing wear and loosening of the attachment.

Figure 12:
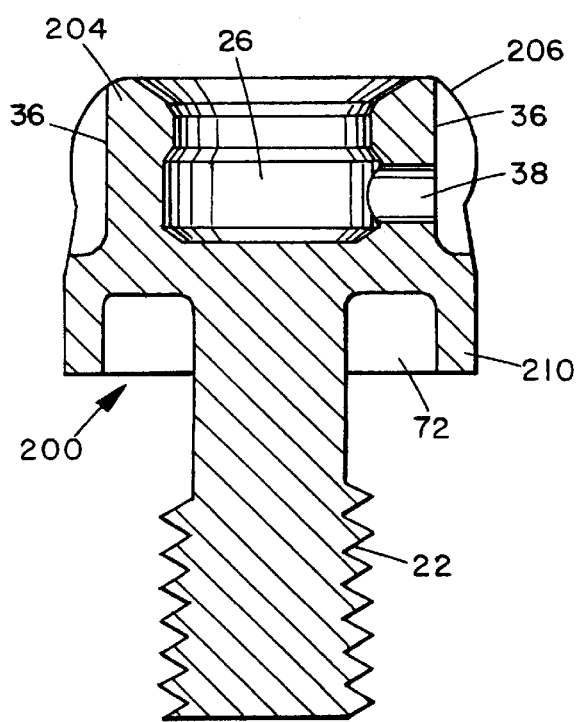
FIG. 12 is a sectional view of a female element of a dental attachment assembly according to another embodiment of the invention.

FIG. 12 illustrates a female or abutment element 200 according to another embodiment of the invention. Element 200 is similar to that of FIGS. 1 to 4, and like reference numerals refer to like parts as appropriate. This abutment element 200 is designed for snap engagement with the male element 202 of FIG. 14. Male element 202 is similar to the male element of FIGS. 2 to 4, and like reference numerals have been used as appropriate. However, in the embodiment of FIGS. 12 and 14, the assembly has an outside snap retention in addition to the inside snap retention provided between socket 26 and retention head 28.

Figure 13:
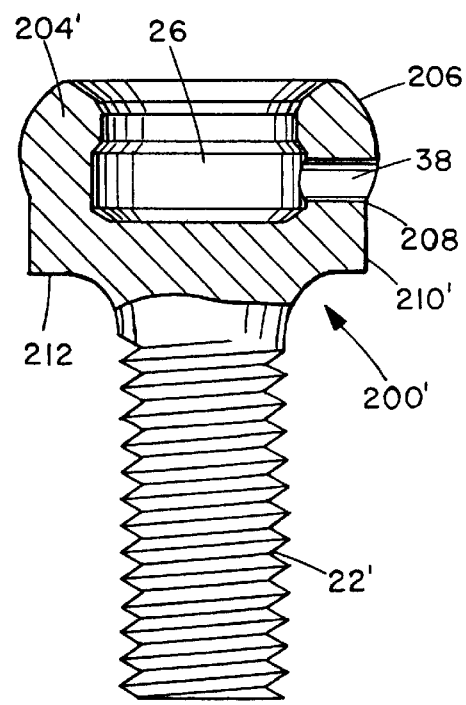
FIG. 13 is a sectional view similar to FIG. 12 illustrating another embodiment of the invention with a root anchor attachment.

As in the first embodiment, the female or abutment element 200 is of relatively strong material such as titanium coated with titanium nitride, or the like. Element 200 has an enlarged upper end portion 204 having an upwardly facing socket 26 and a downwardly depending, threaded stem 22 for attachment in an implant fixture (not illustrated). The upwardly facing socket is of suitable shape and dimensions for releasable snap engagement with the downwardly depending, plastic retention head 28 of male element 202, as in the first embodiment. The lower face of end portion 204 has a hex indent 72 for engagement with an upper hex formation on the implant fixture. FIG. 13 illustrates a modified female element 200' in which the hex indent 72 is eliminated. Element 200' is designed for direct cementation in the prepared bore in a tooth root of an upper or lower dental arch. Element 200' has a shorter head portion 204' than that of FIG. 12, but is otherwise similar to the abutment element 200 of FIG. 12, and like reference numerals have been used as appropriate. The external notches 36 are eliminated in this case since the element 200' is cemented into a tooth root bore and does not need an insertion tool.

The head or upper end portion 204 of element 200 has an upper, convex or outwardly bulging locator portion 206 which extends down to an indent or notch 208. A generally cylindrical skirt portion 210 extends downwardly from notch 208. The modified female element 200' also has an upper, outwardly bulging locator portion 206 and notch 208, followed by a shorter cylindrical portion 210' leading down to the lower, substantially flat end face 212 of the head or end portion 204'.

Figure 14:
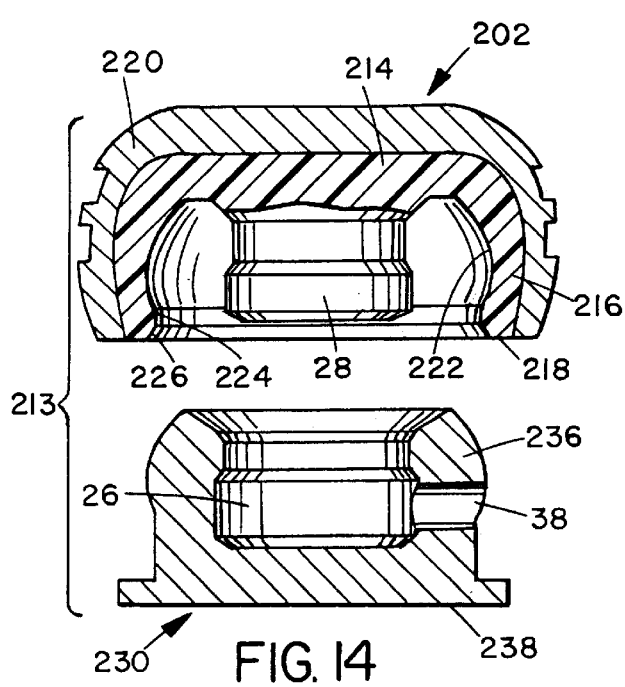
FIG. 14 is a partial section through the male element of the attachment assembly, with the male hingedly attached to a cap, and a locator plastic pattern shown separately.

FIG. 14 illustrates a denture attachment 213 comprising male element 202, and a modified female element 230 comprising a locator plastic pattern. The male element may be secured to any one of the female or abutment elements 200, 200', or 230 of FIGS. 12 to 14.

The male element 202 is of a material having some resilience, preferably nylon plastic, and is generally cup shaped. The upper surface 214 is generally flat, and a skirt 216 projects downwardly from the upper surface to surround the retention head 28. The retention head has an outer shape substantially matching that of socket 26, and is designed for snap engagement in the socket. The skirt 216 has a lower end 218 which projects downwardly below the lower end of retention head 28. The outer surface of the skirt is convex or rounded for snap-fit, swiveling engagement in a cavity of corresponding shape in cap 220.

The inner surface of skirt 216 has an upper, concave or inwardly bulging portion 222, an annular ring portion 224 of reduced diameter, and a lower, outwardly tapered rim 226, and is designed for releasable, snap engagement over the convex portion 206 of the female element 200 or 200'. As the male element is pushed down towards female element 200 or 200', the lower end 218 will first contact the outwardly tapering upper end of the convex portion 206. This will cause the skirt to flex outwardly over the outwardly bulging portion, and then snap back inwardly so that the annular ring 224 rests in notch 208. At the same time, the upper end of the convex portion engaging the skirt will have a centering or locating action, aligning the retention head 28 properly with the socket 26. As the skirt snaps over the outer surface of the upper end portion 204, the retention head 28 will simultaneously snap into the socket 26, providing both an outer and an inner retention of the dental appliance on the female element.

FIG. 14 illustrates another modified female or locator element 230, which is similar to that of FIGS. 12 and 13 except for the elimination of the threaded stem 22,22', and like reference numerals have been used for like parts of locator element 230 as appropriate. Locator element 230 is a plastic pattern for casting with a gold coping directly on the exposed superior surface of a root 232, as in FIG. 15, or several plastic patterns may be cast onto a bar 234 secured to several implants, as in FIG. 16. The female element 230 has a head portion 236 identical to the upper end portions 204, 204' of FIGS. 12 and 13, and a flat lower end face 238 of diameter matching that of the upper end of root 232.

Figure 16:
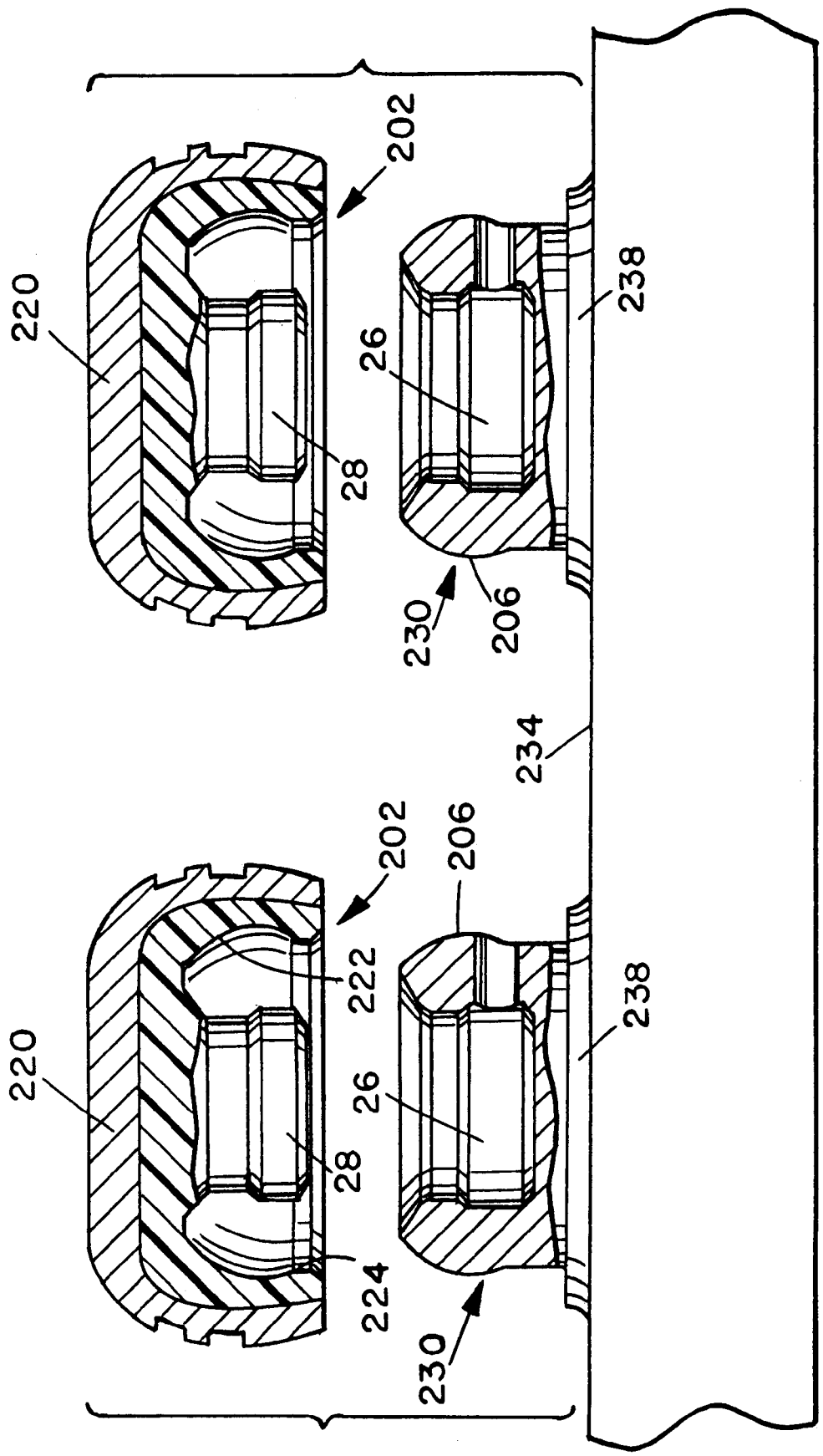
FIG. 16 is a sectional view, illustrating two female elements or plastic patterns cast onto a bar and aligned with two male elements.

Male element 202 may be snap engaged onto any of the three female or locator elements 200,200', or 230, which in turn may be secured to an implant, directly into a prepared bore in a tooth root, or to the upper end of an existing root 232. Locator elements 230 may also be cast at predetermined positions on a bar 234 which is secured to a plurality of dental implants in a known manner, and may be snap engaged with corresponding male elements 202 secured in a denture as indicated in FIG. 16.

Locator element 230 is initially formed as a plastic pattern, which is cast into metal in a dental lab on stone model of a root, and is then connected over the upper surface of the root, which is first flattened by the dentist. Alternatively, the locator element is cast onto a bar 234 as in FIG. 16.

In each of the alternatives illustrated in FIGS. 12 to 16, better retention is provided by the inner and outer snap engagement of the male element onto the female or locator element. At the same time, all the advantages of the previous embodiments are obtained, since the skirt will engage over the initially outwardly tapering bulge on the female element to center the retention head on the socket as the head is urged towards the female element, in a similar manner to that illustrated in FIG. 3. The improved retention will also reduce wear problems, since the outer, snap-engaging surfaces will still provide retention even if the retention head wears out over time. This can double the lifetime of the attachment assembly. The outer snap engaging surfaces 206,222 are preferably designed to allow a small amount of vertical movement of the male element relative to the female or locator element.

Figure 17:
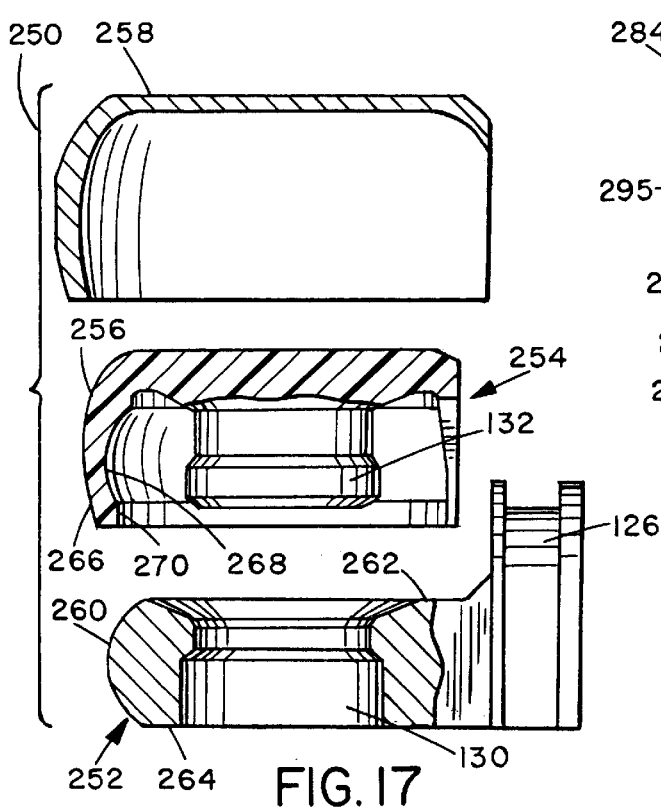
FIG. 17 is a sectional view of a partial denture attachment assembly according to another embodiment of the invention, with the parts separated.

FIG. 17 illustrates a denture attachment or anchor assembly 250 according to another embodiment of the invention. The attachment assembly 250 in this case is designed for attachment to an abutment tooth, similar to the embodiment of FIGS. 9 and 10 above, and like reference numerals have been used for like parts as appropriate. Additionally, the embodiment of FIG. 17 has both inside and outside retention, like that of FIGS. 12 to 16.

The assembly 250 basically comprises a female or locator element 252 having a distal extension 126 which is secured in a suitable slot provided in an adjacent abutment tooth (not illustrated), and a male element 254 for releasable snap engagement with female element 252. Female element 252 has a through bore or socket 130 which is shaped for releasable snap engagement with a retention head 132 of the male element 254. The male element 254 has an outer surface 256 which is rounded for swiveling engagement in a cap 258 which is welded in a suitable recess in a dental appliance (not illustrated).

The female or locator element 252 has an outwardly bulging or convex outer surface 260 which extends from the upper end 262 to the lower end 264 of element 252. The male element 254 is generally cup shaped, as in the previous embodiments, and has a downwardly projecting skirt 266 surrounding retention head 132 and extending down below the lower end of head 132. The inner surface of the skirt has an inwardly bulging or concave portion 268 for mating snap engagement with the convex outer surface 260 of the female element 252. Concave portion 268 terminates above the lower end of the skirt, and an annular rim portion 270 projects downwardly from concave portion 268.

In this embodiment, the entire outer surface of the female element is used for snap engagement with the inner concave surface on the male skirt. As the male element is moved towards the female or locator element, the lower end of the skirt will first contact the upper, outwardly curving portion of the outer surface 260, and the skirt will be biased outwardly over the bulge, snapping inwardly over surface 260 as soon as it clears the maximum diameter portion of the bulge. At the same time, the retention head 132 will move into snap engagement in socket 130. This provides all the advantages of increased retention and increased lifetime of the attachment as in the previous embodiment. Additionally, the partial denture attachment allows the entire outer surface of the female element to be used for the snap engagement. The outer surface curves continuously from the lower end up into the rim of the socket 130, avoiding any sharp edges which could potentially damage the resilient male element. This will also increase lifetime of the attachment.

Figure 18:
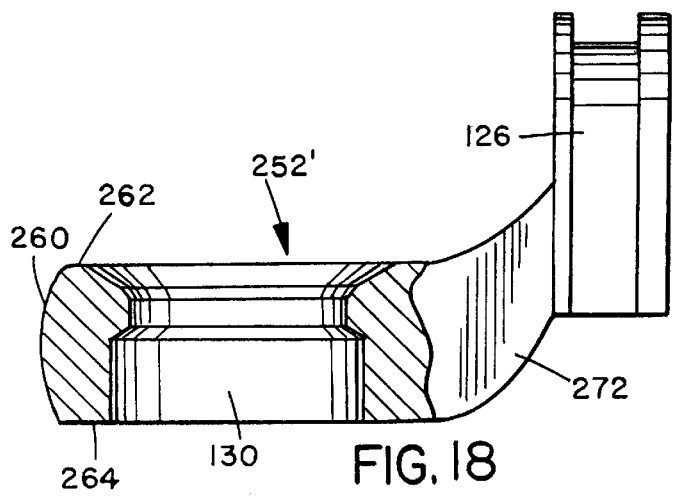
FIG. 18 is a sectional view of a modified partial denture socket element for use with the assembly of FIG. 17.

FIG. 18 illustrates a modified female element 252' for engagement with the same male element 254 as in FIG. 17, but with a lower angle extension 272 as may be required in some cases depending on the adjacent tooth placement. The female element 252' is otherwise similar to that of FIG. 17, and like reference numerals have been used as appropriate.

Figure 19:
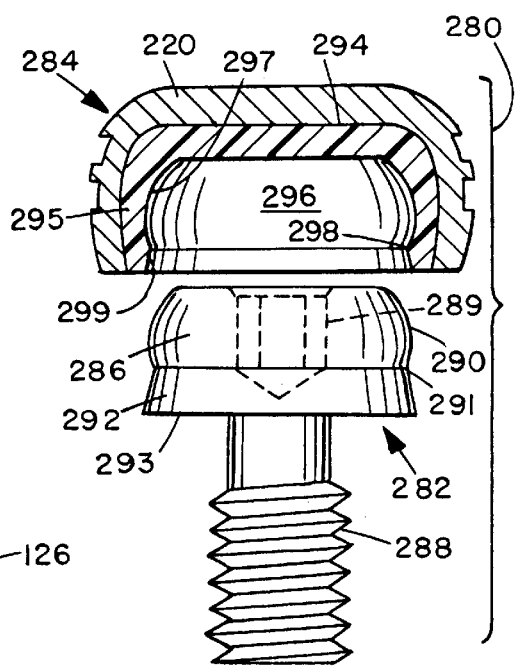
FIG. 19 is a partial sectional view of the attachment members of a dental attachment assembly according to a further embodiment of the invention.

In the embodiments of FIGS. 12 to 18, several attachment assemblies were described which provided both inside and outside snap retention of a male element on a female locator element, as well as location and centering of the male element over the female socket so that the retention head was properly aligned prior to engagement. FIG. 19 illustrates an alternative denture attachment or anchor assembly 280 in which the inner snap engagement is eliminated, and an external snap retention only is provided. This attachment may be used, for example, in cases where less retention force is required, and has advantages over the inner snap only arrangement of FIGS. 1 to 11 since it will be less liable to wear of the snap engaging surfaces.

Anchor assembly 280 comprises a first, locator or abutment member 282 and a second, snap-on or retention member 284, which replaces the male elements of the previous embodiments. The locator or abutment member 282 has a head 286 and a threaded stem 288 depending downwardly from head 286 for threaded engagement in a hexed implant (not illustrated). The head 286 has a hex-shaped indent or socket 289 extending downwardly from its upper end, for engagement with a suitable tool for securing member 282 to an implant. The outer surface of the head has an outwardly bulging or convex portion 290, equivalent to convex portions 206 of the embodiments of FIGS. 12 to 16, an indent 291, and an outwardly tapered lower end portion 292. The lower end 293 of the head may have a hex indent (not illustrated) similar to that of FIGS. 2 and 12, for engaging a corresponding hex formation on a hex implant.

The second, snap-on member 284 is generally cup-shaped as are the male elements of the previous embodiments, but the retention head is completely eliminated. The snap-on member 284 has a generally flat upper end face 294 and a downwardly depending skirt 295 forming an inner cavity 296 for engaging over the head of locator member 282. The outer surface of member 284 is rounded for swivel engagement in cap 220, which is identical to the cap of FIGS. 12 to 16. The inner surface of skirt 295 has an upper, concave or inwardly bulging portion 297, a minimum diameter, circular ridge 298, and an outwardly tapered lower rim 299 below ridge 298, with the shape and dimensions substantially matching those of the outer surface of head 286. As in the previous embodiments, snap-on member is of resilient, durable material such as nylon plastic.

As the snap-on member is moved downwardly towards the head, the outwardly tapered rim 299 will first contact the inwardly curved upper regions of the convex portion 290 of the head. Further downward motion will force the minimum diameter ridge 298 to flex outwardly to clear the maximum diameter part of convex portion or bulge 290, after which it will snap back into indent 291. This snap engagement will releasably retain the snap-on member on the head unless positively removed, thus securing a dental appliance to the implant.

Figure 20:
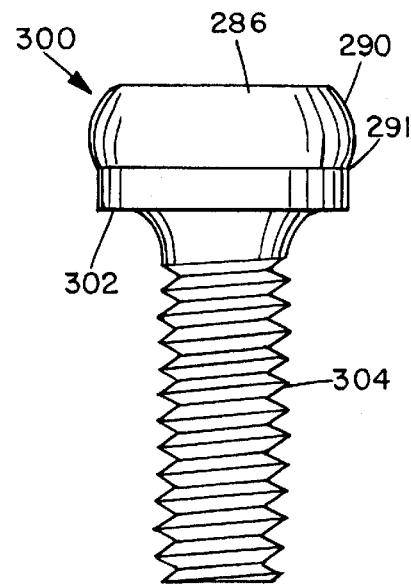
FIG. 20 is a side elevational view of a modified locator root anchor attachment for use with the snap-on locator member of FIG. 19.

FIG. 20 illustrates a modified locator or attachment member 300 which is similar to that of FIG. 19, and like reference numerals have been used for like parts as appropriate. The locator member 300 has locator and snap-engaging portions 290,291 identical to those of FIG. 19, and is designed for snap engagement with the same snap-on member 284. However, the head 286 has a flat lower end face 302 and a threaded stem 304 for direct cementation into a prepared bore in a tooth root of an upper or lower dental arch.

Figure 15:
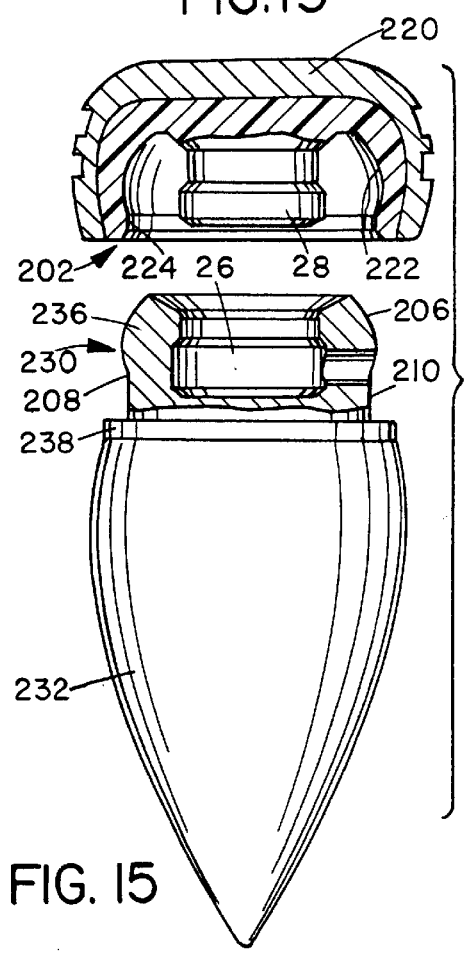
FIG. 15 is a view similar to FIG. 14 showing the locator plastic pattern cast in metal onto a root.

It will be understood that the locator member with outside retention only may also be provided without a threaded stem, as in FIGS. 15 and 16, so that it may be secured directly to a flattened upper end of a root or onto a denture bar. The partial denture of FIGS. 17 and 18 may also be modified to provide outside retention only.

The use of an outside snap engagement, rather than an inside snap engagement into a socket in a female abutment element, has advantages since there is then no retention head which is liable to wear as a result of bumping against end faces of the abutment element if attempts are made to insert it when it is out of alignment with the socket. The snap-engaging convex and concave surfaces of the members in FIGS. 19 and 20 are much less susceptible to damage and wear, and will last longer than an attachment assembly with inside retention only.

In each of the above embodiments, a male or snap-on attachment is provided which is secured at one end to a cap and at the other end to a female or locator element, with both ends of the male having some freedom of movement relative to the part to which it is secured. In the embodiments of FIGS. 1 to 18, the male element has a central retention head for releasable snap engagement in a socket in a female element, and a downwardly depending skirt surrounding the head along part or all of its length. In the embodiments of FIGS. 1 to 10, the skirt extends beyond the end of the head, and acts together with a tapered locating surface on the female element to provide a self-alignment of the male with the female socket as the parts are secured together. This reduces or avoids the risk of the retention head repeatedly impacting against the edge of the socket when re-inserted, which could ultimately damage the head and render it inoperative.

In each of the embodiments, the male or snap-on element has a skirt which contacts an initially outwardly tapering surface on the female or locator element to provide a self-alignment of the parts. In FIGS. 1 to 11, the alignment is provided in conjunction with an internal snap engagement between the parts. In FIGS. 12 to 18, the alignment or locator function is combined with both an internal and an external snap engagement, for increased retention force and increased effective lifetime of the parts. In FIGS. 19 and 20, the locator function is combined with outside snap retention only.

Although some preferred embodiments of the invention have been described above by way of example only, it will be understood by those skilled in the field that modifications may be made to the disclosed embodiment without departing form the scope of the invention, which is defined by the appended claims.

We claim:

1. A dental attachment assembly, comprising:

an abutment member for attachment to a tooth root, implant, or adjacent tooth, the abutment member having an upper end, and an outer locating surface portion projecting downwardly from the upper end, the outer locating surface portion being positioned to project above a tissue level when the abutment member is secured in a tooth root or implant;

a male member for attachment to the abutment member, the male member having an upper end comprising a swivel joint for swivel engagement within a cap in a recess in a dental appliance, and a skirt projecting from the upper end of the male member for engagement over the outer locating surface of the abutment member, the skirt having a rounded, convex outer surface;

the abutment member and male member having mateable snap-engaging formations for releasable snap engagement when the male member is attached to the abutment member; the outer locating surface portion being outwardly tapered at least adjacent the upper end of the abutment member for centering the male member over the abutment member as the members are secured together; and a cap for securing in a recess in a dental appliance, the cap having a cavity for containing said swivel joint, the cavity having a rounded, concave inner surface for releasable snap engagement over the rounded outer surface of the skirt, the swivel joint and cap cavity together comprising means for permitting swivelling of the cap over the male member relative to the dental appliance.

2. The assembly as claimed in claim 1, wherein the abutment member has a socket projecting inwardly from the upper end, of the abutment member and a retention head projects from the upper end of the male member for releasable snap engagement in the socket.

3. The assembly as claimed in claim 2, wherein the retention head has a lower end, and the skirt extends downwardly beyond the lower end of the retention head, whereby the skirt will contact the abutment member before the lower end of the retention head reaches the socket on re-insertion of the male member into the abutment member.

4. The assembly as claimed in claim 2, wherein the retention head does not project downwardly beyond the lower end of the skirt, whereby the lower end of the skirt contacts the abutment member prior to any other part of the attachment assembly.

5. The assembly as claimed in claim 2, wherein the abutment member has a weep hole connecting the socket to the outside of the abutment member for allowing saliva the escape.

6. The assembly as claimed in claim 1, wherein the outer locating surface portion has an outward taper from said upper end and terminates at a predetermined location above the tissue level when the abutment member is secured in a patient's mouth.

7. The assembly as claimed in claim 1, wherein the abutment member comprises a generally cylindrical head having a lower end spaced below said upper end.

8. The assembly as claimed in claim 1, wherein the skirt has an inner surface of predetermined height which is concave and does not contact the outer locating surface portion of the abutment member along at least a major portion of the height of the inner surface when the male and abutment members are secured together.

9. The assembly as claimed in claim 1, wherein the outer locating surface portion of the abutment member has a pair of diametrically opposed elongated notches for engagement with an insertion tool for engaging the abutment member with an implant.

10. The assembly as claimed in claim 1, wherein the abutment member comprises means for attachment to a non-hexed implant, and the abutment member has a minimum height of 1.75 mm.

11. The assembly as claimed in claim 1, wherein the abutment member comprises means for attachment to a hexed implant, and the abutment member has a minimum height of 2.75 mm.

12. The assembly as claimed in claim 1, wherein the abutment member comprises a generally cylindrical head having a convex outer surface portion adjacent said upper end, and the male member is generally cup-shaped with an internal cavity for fitting over said head, the skirt having a concave inner surface portion for snap engagement over said convex outer surface portion to releasably secure the members together, said convex and concave surface portions comprising said mateable snap engaging formations.

13. The assembly as claimed in claim 1, wherein the abutment member has a head portion at the upper end and a shaft depending downwardly from the head portion.

14. The assembly as claimed in claim 13, wherein the shaft is at a predetermined angle to the head portion.

15. The assembly as claimed in claim 14, including a plurality of abutment members for selective engagement with a tooth root or implant, including a first abutment member having a shaft aligned with said head portion, a second, angled abutment member having a shaft at an angle of 10° to said head portion, and a third, angled abutment member having a shaft at an angle of 20° to said head portion.

16. The assembly as claimed in claim 1, wherein the abutment member comprises a head portion having said upper end and a lower end, and a distal extension projecting from said head portion for attaching the abutment member to an abutment tooth, the skirt of the male member having a slot for fitting over said distal extension.

17. The assembly as claimed in claim 16, wherein the outer locating surface portion of said head portion is convex.

18. The assembly as claimed in claim 16, wherein said abutment member has a through bore extending from the upper end to said lower end, and the male member has a retention head projecting from its upper end for releasable snap engagement in said through bore.

19. The assembly as claimed in claim 18, wherein said skirt has a lower end extending beyond said retention head for contacting said abutment member before said retention head reaches the upper end of said abutment member.

20. The assembly as claimed in claim 19, wherein said skirt and said outer locating surface portion together comprise alignment means for aligning said retention head with said through bore as the male and abutment members are secured together.

21. A dental attachment assembly, comprising:
an abutment member for attachment to a tooth root, implant, or adjacent tooth, the abutment member having an upper end, a socket projecting inwardly from the upper end, and an outer locating surface portion projecting downwardly from the upper end, the outer locating surface portion being positioned to project above a tissue level when the abutment member is secured in a tooth root or implant;
a male member for attachment to the abutment member, the male member having an upper end comprising a swivel joint for swivel engagement within a cap in a recess in a dental appliance, a skirt projecting from the upper end of the male member for engagement over the outer locating surface of the abutment member, and a retention head projecting from the upper end of the male member;
the outer locating surface portion being outwardly tapered at least adjacent the upper end of the abutment member for centering the male member over the abutment member as the members are secured together;
a cap for securing in a recess in a dental appliance, the cap having a cavity for containing said swivel joint, the swivel joint and cap cavity together comprising means for permitting swivelling of the cap over the male member relative to the dental appliance; and
the outer locating surface portion of the abutment member being convex and the skirt has an inner surface with concave portion matching said convex outer surface portion of said abutment member, said convex outer surface portion and concave portion comprising means for releasable snap engagement of the skirt over the outer locating surface portion of the head, whereby both an inner and an outer snap retention of the male member on the abutment member is provided.

22. A method of anchoring a dental appliance in a patient's mouth, comprising the steps of:
securing an abutment member at a predetermined position in a patient's mouth with a head facing upwardly and a predetermined portion of the head projecting above a gum line, the predetermined portion having an outer locating surface;
securing a cap in a recess in a dental appliance, the cap having a cavity with a rounded, concave inner surface portion;
releasably snap engaging one end of a male retention member in the cavity in the cap, the cap engaging end having a rounded, concave outer surface for snap engagement in the cavity whereby a skirt on the male retention member projects downwardly from the appliance and a swivel joint is provided between the cap and male retention member permitting swiveling of the cap over the male retention member;
positioning the dental appliance in the mouth and moving the skirt downwardly towards the abutment member;
engaging the skirt with the outer locating surface of the head to align the male retention member with the head; and
urging the male retention member downwardly into snap engagement with the head.

23. A dental attachment assembly, comprising:
a first, abutment member for attachment to a tooth root, implant, or adjacent tooth, the abutment member having a head having an upper end and an outer locator surface portion projecting downwardly from the upper end and positioned to project above a tissue level when the abutment member is secured in a tooth root or implant;
a second, retention member for releasable snap engagement with the abutment member, the retention member comprising part of a swivel joint for swivel engagement in a recess in a dental appliance, and being generally cup-shaped with an upper end and a peripheral skirt projecting downwardly from the upper end, the skirt having an inner surface for engagement over said outer locator surface portion of said abutment member;
the outer locator surface portion of the abutment member and the inner surface of the skirt having mateable snap-engaging formations whereby the skirt can be releasably snap engaged over the head to releasably secure the parts together; and
the abutment member having a socket projecting inwardly from the upper end and the male member having a retention head projecting from the upper end for releasable snap engagement in the socket, the skirt surrounding the retention head, whereby both an inner and an outer snap engagement is provided between the abutment member and retention member.

24. The assembly as claimed in claim 23, wherein the outer locator surface portion comprises a convex bulge, and the inner surface of the skirt has a concave portion for snap-engagement over the convex bulge.

25. The assembly as claimed in claim 24, wherein the convex bulge and concave portion each extend around the circumference of the respective head and skirt.

26. The assembly as claimed in claim 23, wherein the abutment member has a threaded stem depending downwardly from the head.

27. The assembly as claimed in claim 23, wherein the head has a flat lower end face for attachment to a root or bar.

28. A dental attachment assembly, comprising:
an abutment member having an upper end and a flat lower end face for attachment to a tooth root or a bar, the abutment member having an outer, generally cylindrical surface and a socket projecting inwardly from the upper end;
a male member having an upper end comprising a swivel joint for swivel engagement within a cap in a recess in a dental appliance, a retention head projecting from the upper end for releasable snap engagement in the socket, and a skirt projecting from the upper end and surrounding the retention head along at least part of the length of the retention head, the skirt having a rounded, convex outer surface; and
a cap for securing in a recess in a dental appliance, the cap having a cavity for containing said swivel joint, the cavity having a rounded, concave inner surface for releasable snap engagement over the rounded outer surface of the skirt, and the swivel joint and cap cavity together comprising means for permitting swiveling of the male member relative to the dental appliance.

* * * * *